US012636486B2

(12) United States Patent (10) Patent No.: US 12,636,486 B2

Qiu (45) Date of Patent: May 26, 2026

(54) LOCALISED TRANSDERMAL IONTOPHORETIC DRUG DELIVERY SYSTEM

(71) Applicant: Shanghai Jingxun Infotech Co., Ltd., Pudong New Area (CN)

(72) Inventor: Huaxuan Qiu, Pudong New Area (CN)

(73) Assignee: SHANGHAI JINGXUN INFOTECH CO., LTD., Pudong New Area (CN)

( * ) Notice: Subject to any disclaimer, the term of this patent is extended or adjusted under 35 U.S.C. 154(b) by 1094 days.

(21) Appl. No.: 17/055,208

(22) PCT Filed: Jul. 12, 2019

(86) PCT No.: PCT/CN2019/095881

§ 371 (c)(1),
(2) Date: Nov. 13, 2020

(87) PCT Pub. No.: WO2019/219096

PCT Pub. Date: Nov. 21, 2019

(65) Prior Publication Data

US 2021/0113829 A1 Apr. 22, 2021

(30) Foreign Application Priority Data

May 14, 2018 (CN) .......................... 201810456482.X

(51) Int. Cl.
*A61N 1/04* (2006.01)
*A61N 1/32* (2006.01)

(52) U.S. Cl.
CPC ......... *A61N 1/0448* (2013.01); *A61N 1/0484* (2013.01); *A61N 1/325* (2013.01)

(58) Field of Classification Search
CPC .... A61N 1/0484; A61N 1/0448; A61N 1/325; A61N 1/0428; A61N 1/303; A61N 1/30
See application file for complete search history.

(56) References Cited

U.S. PATENT DOCUMENTS

| 10,298,163 B2 * | 5/2019 | Vasilev | ..................... H03L 5/00 |
| 2008/0312579 A1 * | 12/2008 | Chang | .................. A61N 1/0412 |
| | | | 264/129 |

(Continued)

FOREIGN PATENT DOCUMENTS

| CN | 101522255 A | 9/2009 |
| CN | 101541374 A | 9/2009 |

(Continued)

OTHER PUBLICATIONS

Int'l Search Report issued Sep. 26, 2019 in Int'l Application No. PCT/CN2019/095881.

(Continued)

*Primary Examiner* — Bhisma Mehta
*Assistant Examiner* — Anna E Vargas
(74) *Attorney, Agent, or Firm* — NKL Law; Bin Lu; Allen Xue

(57) ABSTRACT

A localised transdermal iontophoretic drug delivery system which controls localised transdermal drug delivery doses, transdermal drug delivery depths and transdermal drug delivery speeds is provided. The system includes a power supply, a current driving assembly, an optional switch matrix or multiplexer, and electrode assemblies or an electrode assembly array. The localised transdermal iontophoretic drug delivery system accurately controls a drug delivery current distribution between any electrode combination, so as to locally control a transdermal drug delivery dose, a transdermal drug delivery depth and a transdermal drug delivery speed, in order to implement accurate drug delivery to a user's skin.

21 Claims, 9 Drawing Sheets

(56) References Cited

U.S. PATENT DOCUMENTS

| | | | | |
|---|---|---|---|---|
| 2010/0010418 A1 | | 1/2010 | Nisato | |
| 2010/0036284 A1* | | 2/2010 | Laynes | A61B 5/068 |
| | | | | 600/585 |
| 2010/0076367 A1* | | 3/2010 | Ackermans | A61N 1/30 |
| | | | | 604/20 |
| 2011/0015697 A1* | | 1/2011 | McAdams | A61N 1/205 |
| | | | | 607/50 |
| 2014/0039378 A1* | | 2/2014 | Imran | A61N 1/30 |
| | | | | 604/20 |
| 2016/0089308 A1* | | 3/2016 | Mohammadi | A61K 8/0212 |
| | | | | 604/20 |
| 2017/0354816 A1* | | 12/2017 | Huelman | A61N 1/0484 |

FOREIGN PATENT DOCUMENTS

| | | | | |
|---|---|---|---|---|
| CN | 105435367 A | 3/2016 | | |
| CN | 106995927 A * | 8/2017 | | |
| CN | 108379734 A | 8/2018 | | |
| WO | WO-0224274 A1 * | 3/2002 | ............. | A61N 1/044 |

OTHER PUBLICATIONS

Examination report issued Feb. 5, 2021 in AU Application No. 2019270870.

Office Action issued May 1, 2021 in CN Application No. 201810456482.X.

Office Action issued Sep. 9, 2021 in CN Application No. 201810456482.X.

Written Opinion issued Dec. 17, 2021 in SG Application No. 11202011379X.

Written Opinion issued Dec. 6, 2023 in SG Application No. 11202011379X.

* cited by examiner power source 1..K
current drive assembly
1..N
(optional)
current sensor
on the high
voltage side
connected to controllers
and drivers 1..N
connected to
electrodes 1..N
(optional)
current sensor
on the low
voltage side
F i g.    1
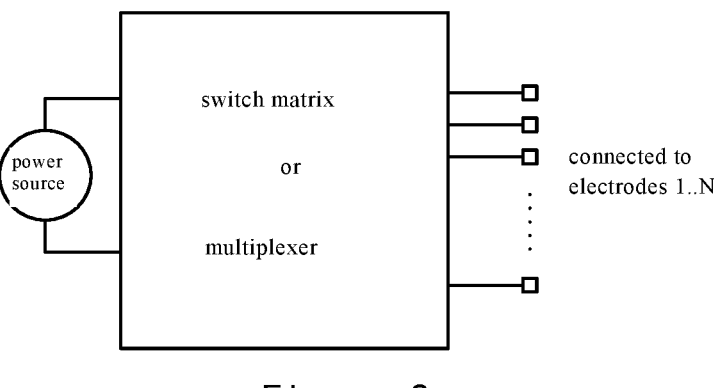
switch matrix
or
multiplexer
power
source
connected to
electrodes 1..N
F i g.    2

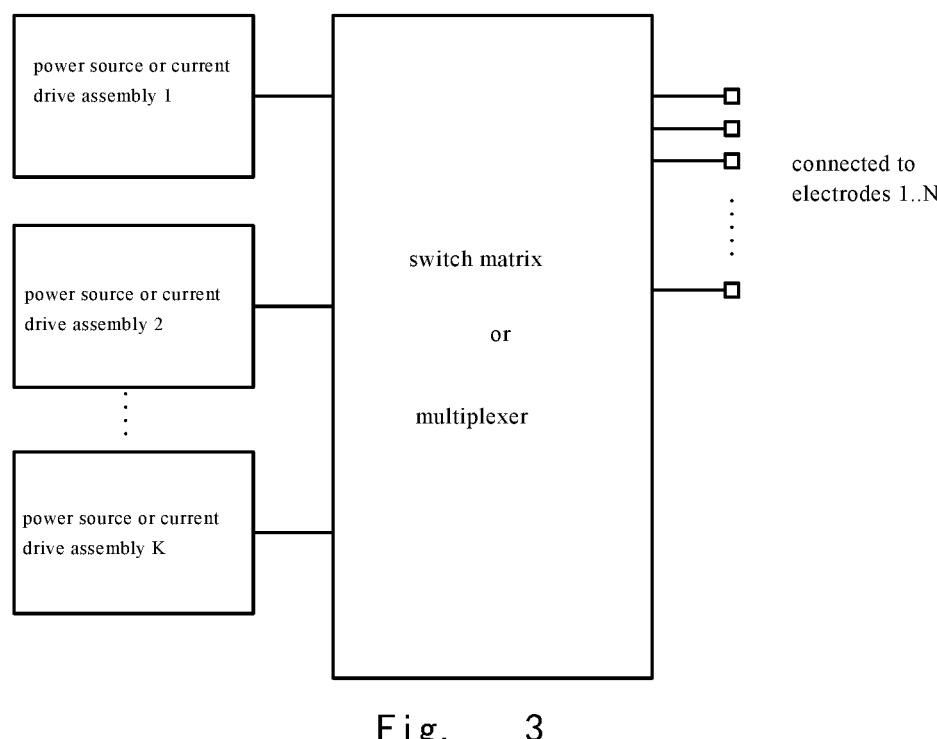
Fig.    3
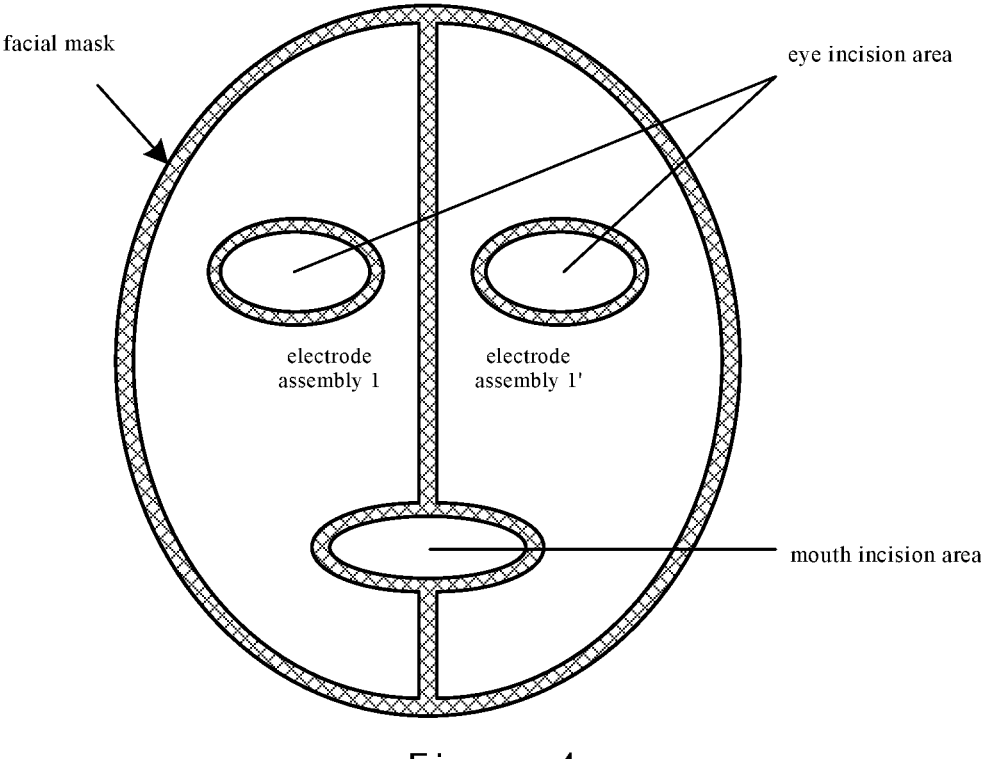
Fig.    4

(facial) distribution diagram of transdermal drug delivery active agent facial mask electrode assembly 2 electrode assembly 2' electrode assembly 1 electrode assembly 1' eye incision area mouth incision area

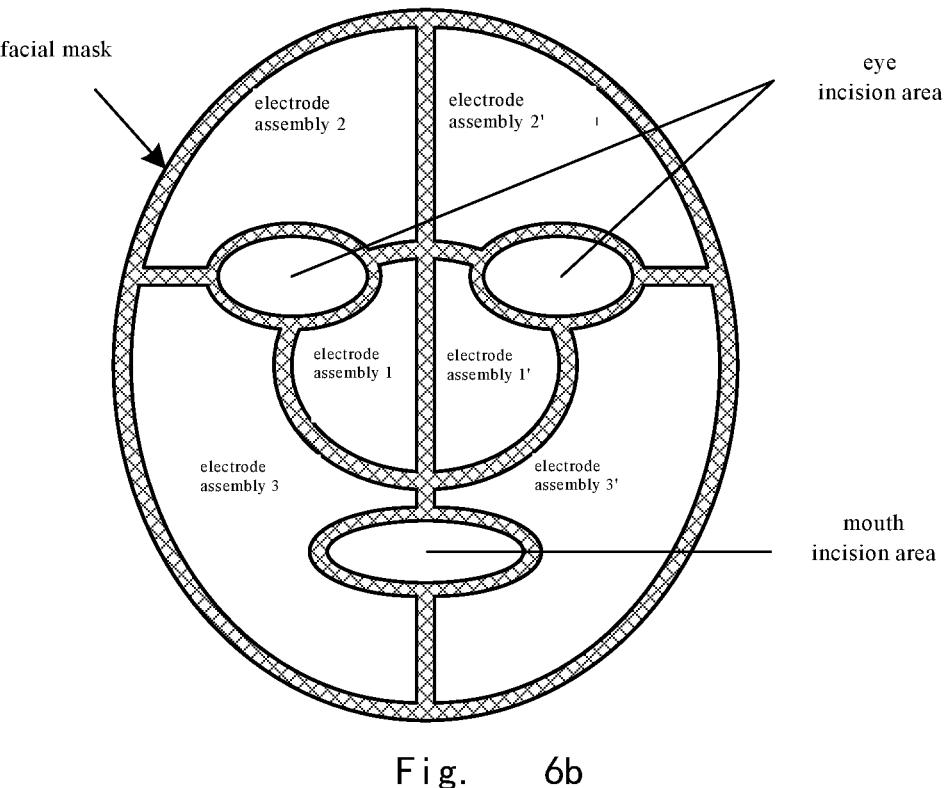
F i g. 6b
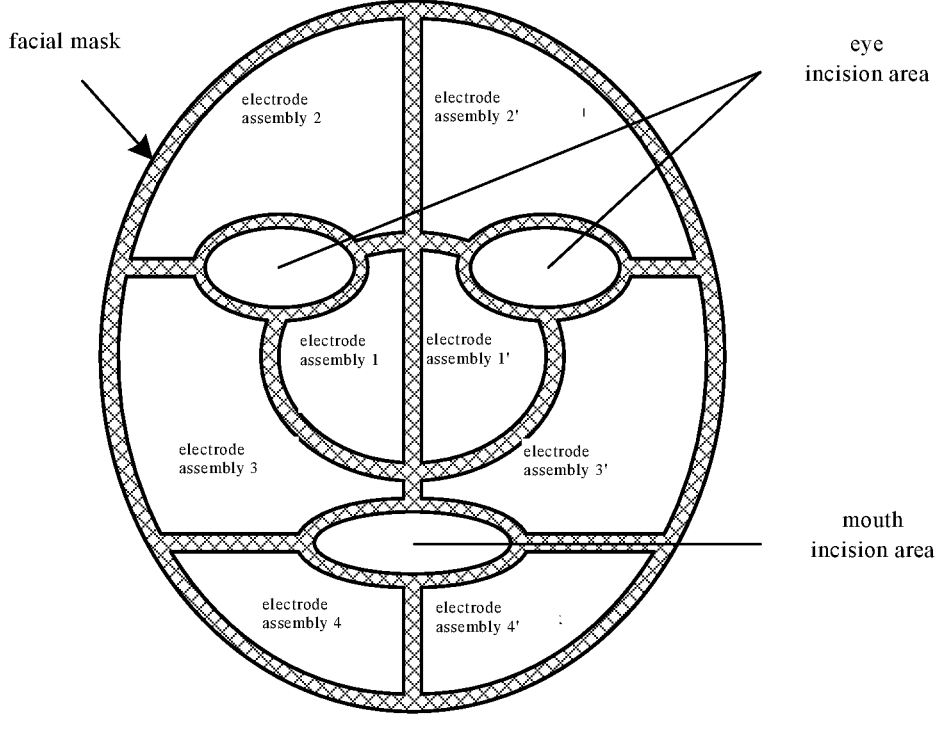
F i g. 6c

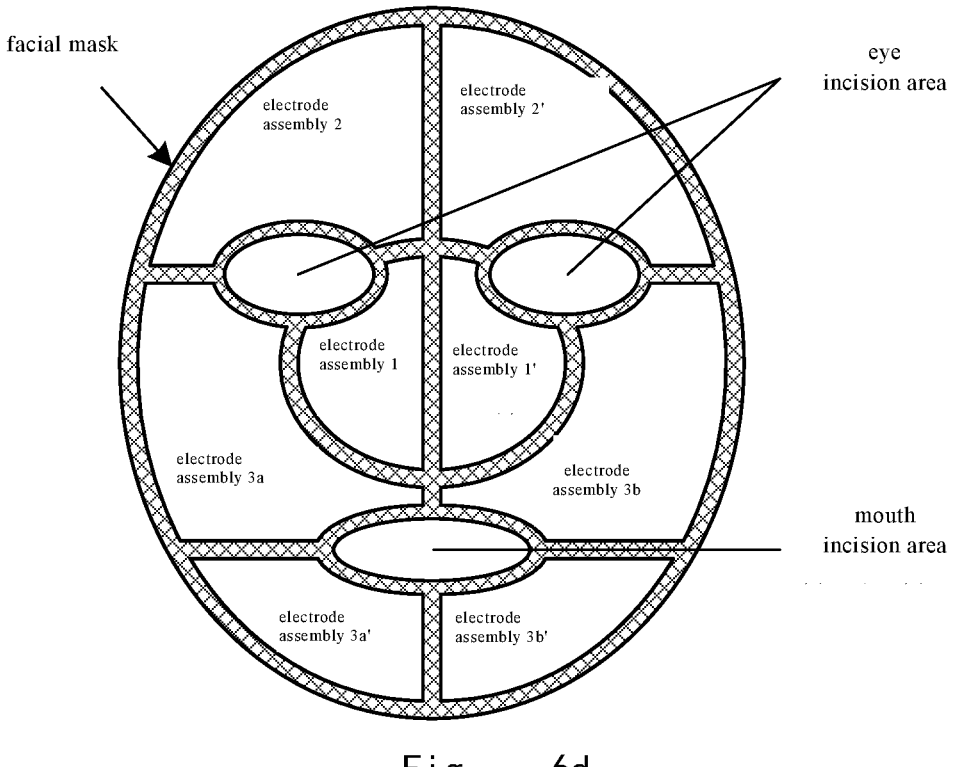
Fig.    6d
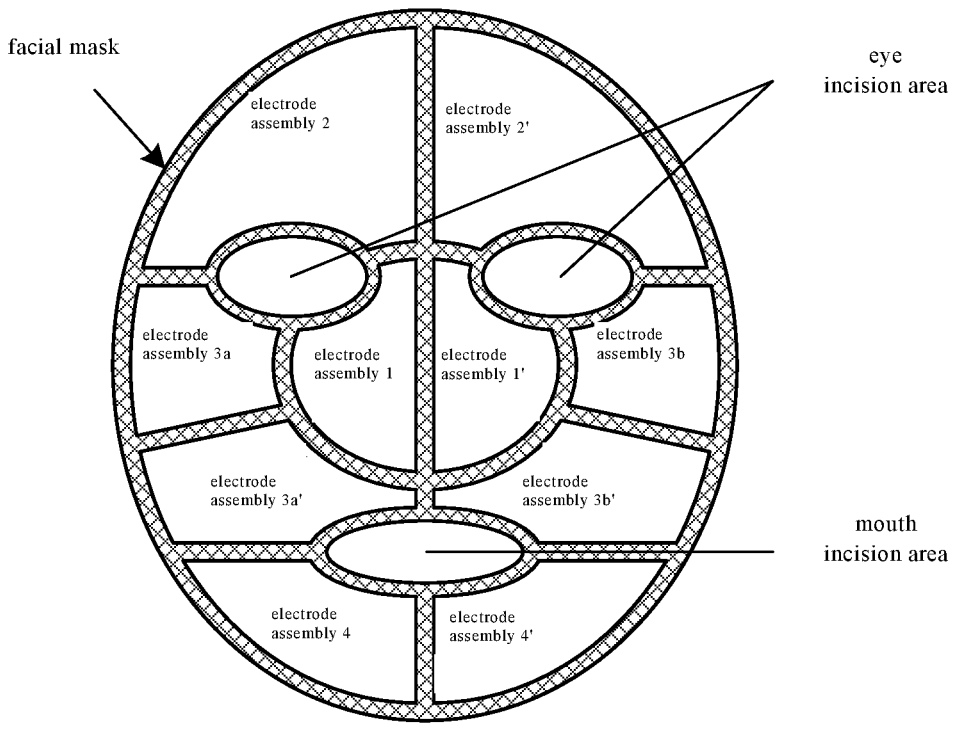
Fig.    6e

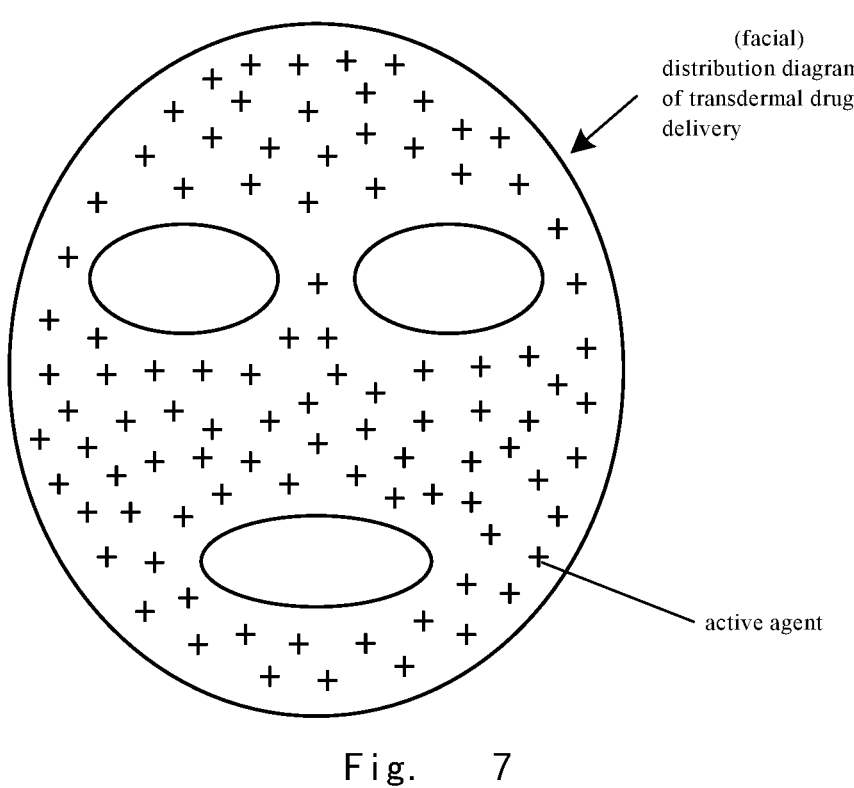
(facial)
distribution diagram
of transdermal drug
delivery
active agent
Fig.    7
sub-electrode assembly in electrode
assembly array matrix
facial mask
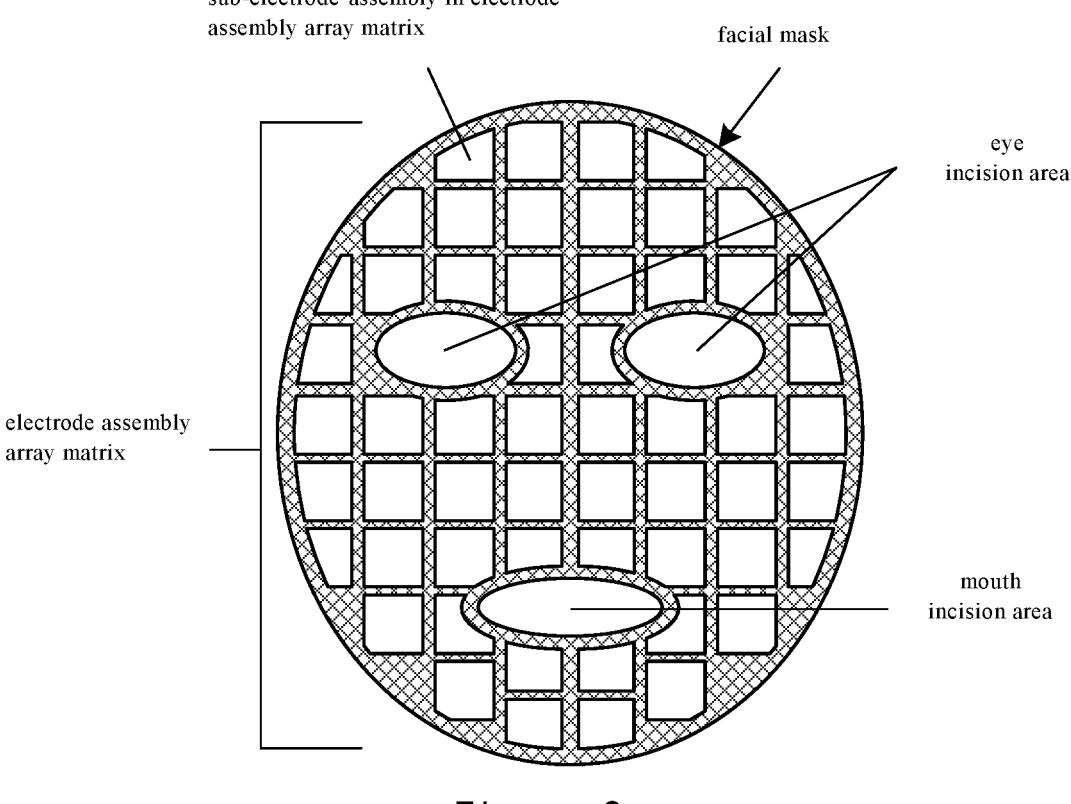
eye
incision area
electrode assembly
array matrix
mouth
incision area
Fig.    8a

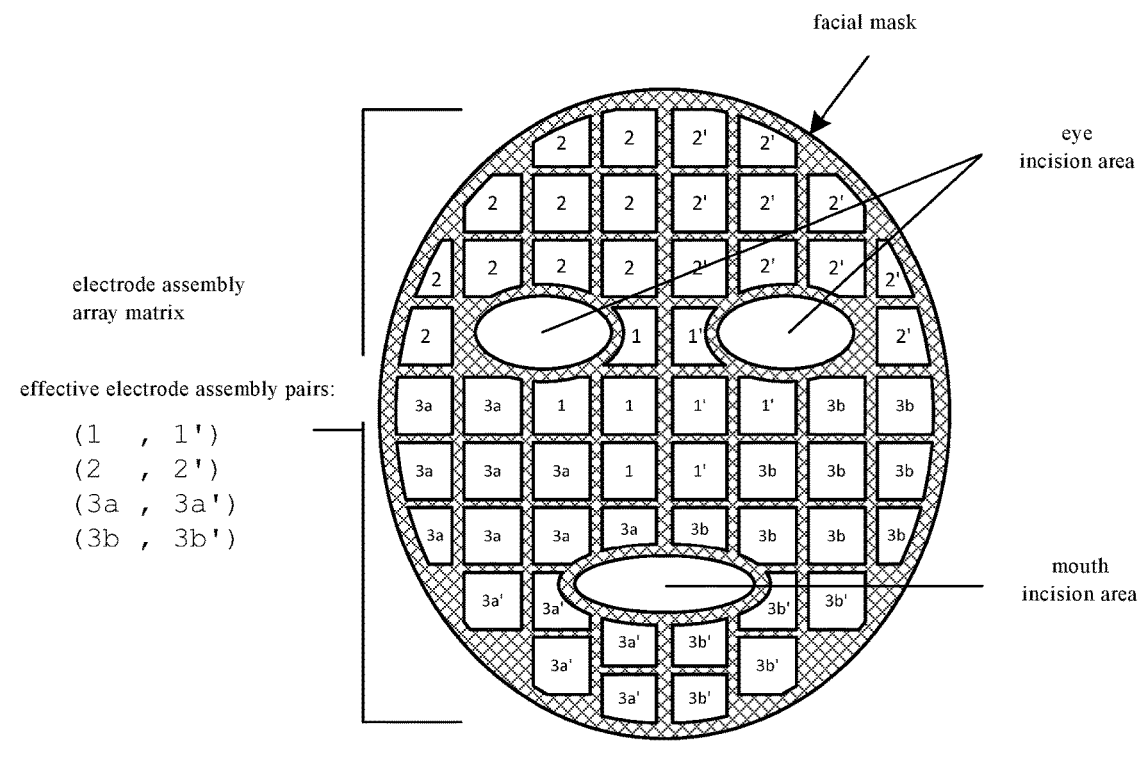
Fig.    8b
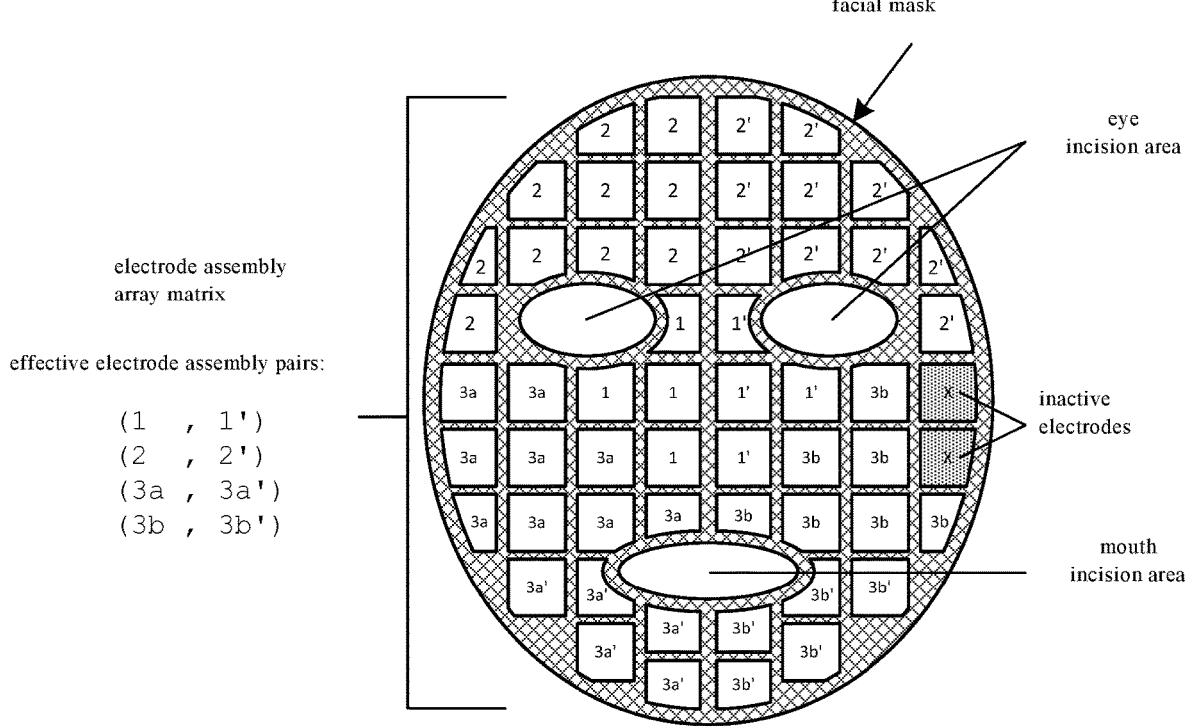
Fig.    8c

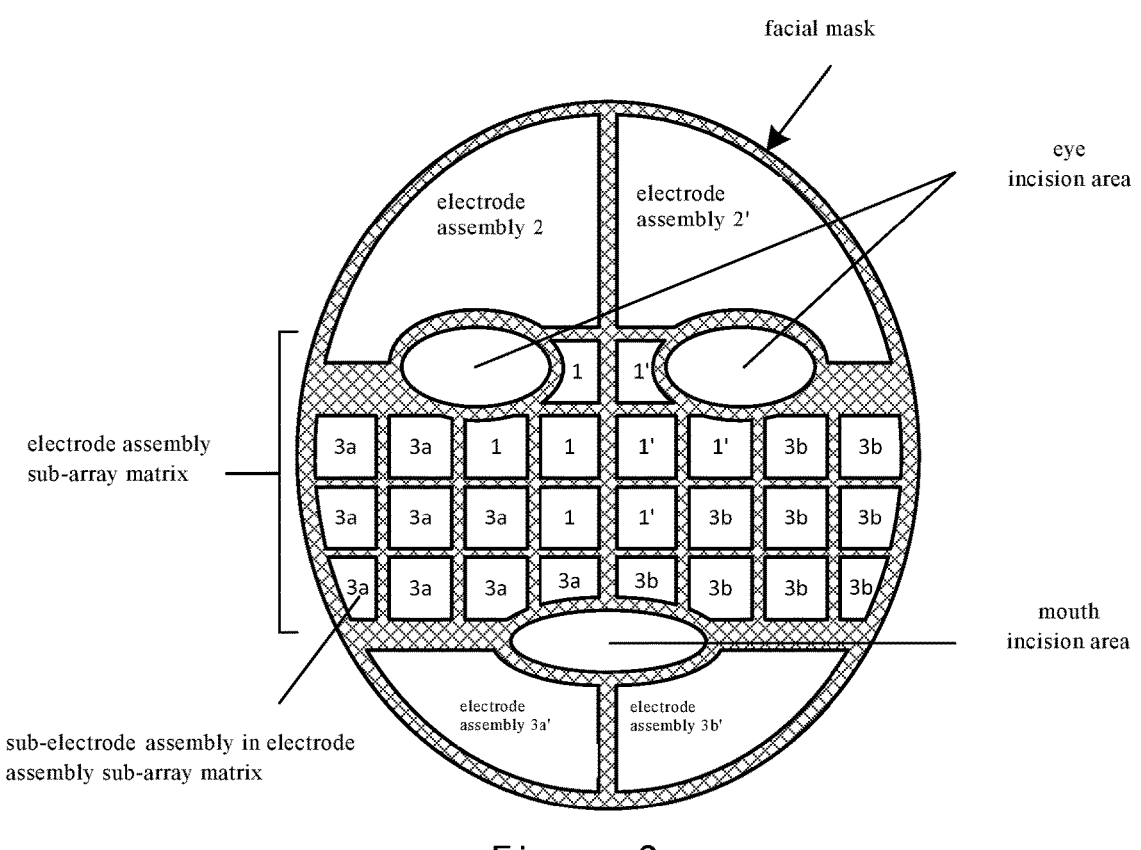
Fig.    9
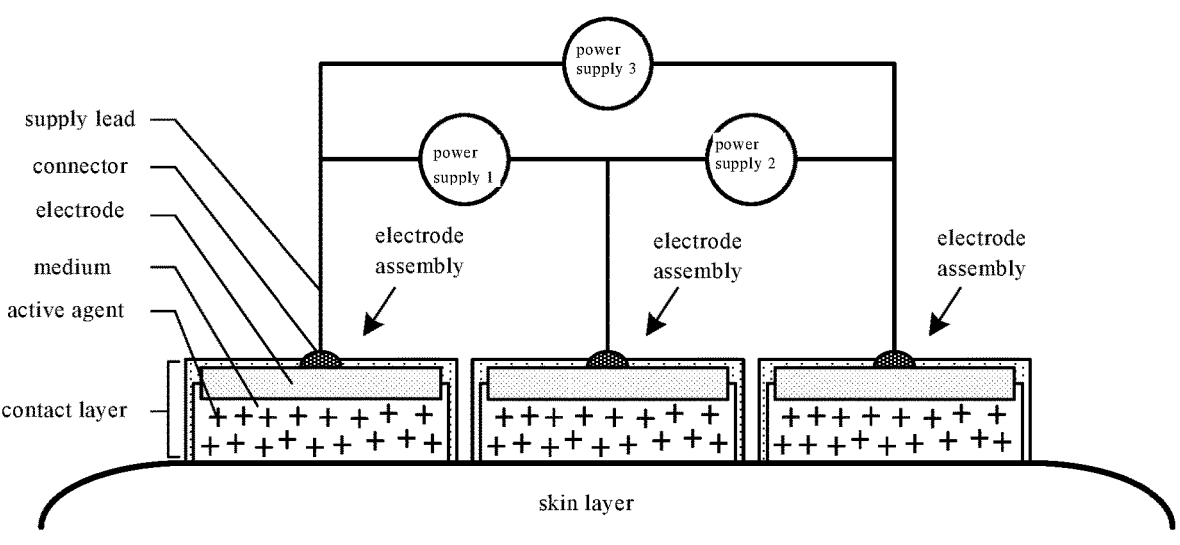
Fig.    10

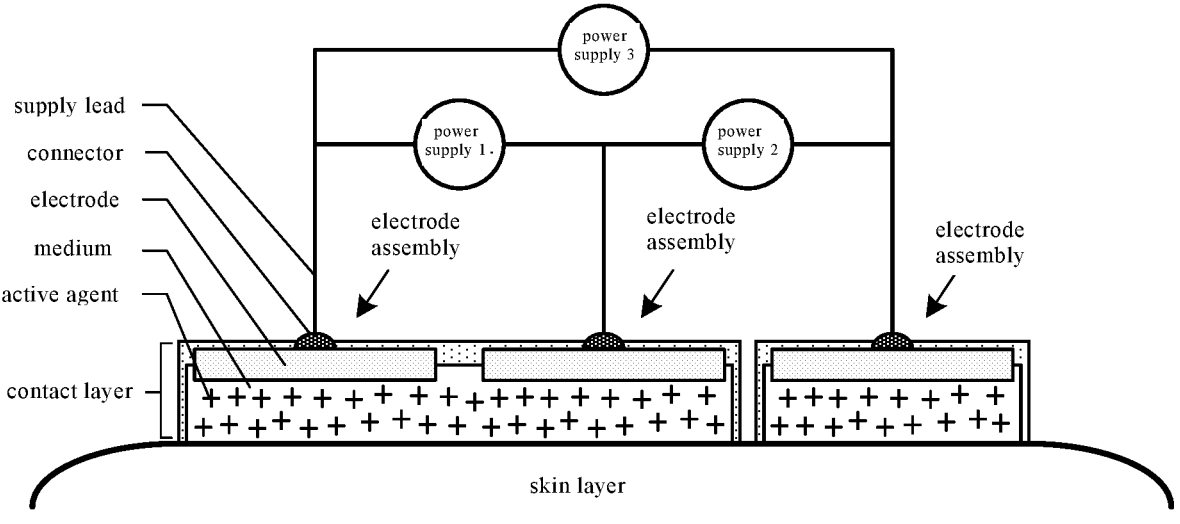
F i g.     11

LOCALISED TRANSDERMAL IONTOPHORETIC DRUG DELIVERY SYSTEM

CROSS-REFERENCE TO RELATED APPLICATIONS

This application is a Section 371 of International Application No. PCT/CN2019/095881, filed Jul. 12, 2019, which was published in the Chinese language on Nov. 21, 2019, under International Publication No. WO 2019/219096 A1, which claims priority under 35 U.S.C. § 119(b) to Chinese Application No. 201810456482.X, filed May 14, 2018, the disclosures of each of which are incorporated herein by reference in their entireties.

FIELD OF INVENTION

The present invention relates to the field of medical equipment, in particular to a localised transdermal iontophoretic drug delivery system.

BACKGROUND OF INVENTION

The love of beauty is a common topic of human beings, especially women. With the improvement of economic level, more and more women pay more attention to their appearance. Among them, skin care as an important part of beauty, accounts for more than half of women's beauty consumption. Skin care has become a science in modern times.

With the increasing pursuit of health and the rapid development of dermatology, medical skin care products with higher safety and efficacy have become an unstoppable trend.

The main purpose of the traditional transdermal iontophoretic drug delivery technology is to deliver the drug through the skin and into the blood, and there is no special requirement for the route of drug delivery through the skin. Therefore, the traditional transdermal delivery systems have two large electrodes and use a voltage between the two electrodes to cause a current flow to introduce the drug. However, considering the characteristic that the current always flows in the path of least resistance, the drug delivery current is very likely to be concentrated only in some small areas of the large electrode. Therefore, the current technology cannot guarantee the uniformity of transdermal drug delivery.

In the field of beauty, it is very important to evenly nourish and moisture the skin. Taking facial skin as an example, the T zone (forehead, nose) of general users is relatively greasy and has enlarged pores. If a large electrode is used to cover the entire face to form a transdermal drug delivery mask, the drug current will selectively avoid areas with higher resistance, resulting in a very uneven distribution of drug delivery. In addition, when the user has a wound on the skin, the delivery current may be concentrated on the wound, not only irritating the wound, but also reducing the ability to deliver the drug to other areas.

In summary, in order to solve the above-mentioned problem of uneven administration due to the great differences in facial skin and skin quality, there is an urgent need in the art to develop an iontophoretic drug delivery system which can be locally controlled in the amount, depth and speed of transdermal drug delivery.

SUMMARY OF INVENTION

The purpose of the present invention is to provide an iontophoretic drug delivery system which can be locally controlled in the amount, depth and speed of transdermal drug delivery.

In a first aspect of the present invention, it provides a localised transdermal iontophoretic drug delivery system, comprising:

(a) an electrode assembly array, wherein the electrode assembly array comprises N electrode assemblies, and N≥3; and each electrode assembly comprises one electrode; and (b) M power sources, wherein the power sources are used for supplying current to the corresponding electrodes or electrode pairs, wherein M is a positive integer from 1 to C(N, 2), wherein C(N, 2) represents a combination number of any 2 elements from N elements (C) or $$C_N^2;$$

wherein, at least two electrodes in the electrode assembly array are provided with a medium containing an electrically charged active agent, and the current pushes the active agent to the skin layer at a time period during which the current has the same polarity as that of the active agent.

In another preferred embodiment, the number of electrodes N is an even number, and the number of power sources M is a positive integer ranging from 2 to N/2.

In another preferred embodiment, the M power sources are used for supplying power to the electrode assembly array in the following manner:

one or more power sources; and multiple current drive assemblies.

In another preferred embodiment, the M power sources are used for supplying power to the electrode assembly array in the following manner:

one or more power sources; and a switch matrix or a multiplexer.

In another preferred embodiment, the M power sources are used for supplying power to the electrode assembly array in the following manner:

one or more power sources;

one or more current drive assemblies;

a switch matrix or a multiplexer.

In another preferred embodiment, the power source simultaneously supplies current to the corresponding electrodes or electrode pairs.

In another preferred embodiment, the power source successively supplies current to the corresponding electrodes or electrode pairs.

In another preferred embodiment, the power source can supply current to the corresponding electrode or electrode pair at different time periods.

In another preferred embodiment, wherein each electrode assembly comprises a corresponding contact layer; wherein, the contact layer is used to store the medium containing an active agent and is connected with electrode fluid.

In another preferred embodiment, each electrode is independently provided with an independent contact layer.

In another preferred embodiment, multiple electrodes share one contact layer.

In another preferred embodiment, each electrode assembly in the electrode assembly array comprises a connector, and the connector connects the electrode assembly to the corresponding power source.

In another preferred embodiment, the connector connects the electrode assembly to the corresponding current drive assembly.

In another preferred embodiment, the connector connects the electrode assembly to the corresponding switch matrix or multiplexer.

In another preferred embodiment, the current is a direct current.

In another preferred embodiment, the current is an alternating current.

In another preferred embodiment, the alternating current has one or more characteristics selected from the following group:

(i) the period is from 1 second to 30 minutes, preferably from 1 second to 15 minutes, more preferably from 1 second to 10 minutes, and most preferably from 1 second to 5 minutes;

(ii) the waveform is a basic waveform between the maximum value and the minimum value, comprising a climbing time period, during which the current increases from the minimum value to the maximum value, or decreases from the maximum value to the minimum value; and (iii) the duty ratio is 5%-95%, preferably 10-80%, more preferably 20-70%.

In another preferred example, during operation, the current between any pair of working electrodes is 0.01-4 mA.

In another preferred embodiment, the electrode assembly array comprises:

an I electrode assembly pair or an I electrode assembly sub-array, which corresponds to the nose area of the face; and an II electrode assembly pair or an II electrode assembly sub-array, which corresponds to the forehead area, cheek area and chin area of the face.

In another preferred embodiment, the I electrode assembly pair is in a non-array form.

In another preferred embodiment, the I electrode assembly sub-array comprises ≥3 electrode assemblies.

In another preferred embodiment, the II electrode assembly pair is in a non-array form.

In another preferred embodiment, the II electrode assembly sub-array comprises ≥3 electrode assemblies.

In another preferred embodiment, the electrode assembly array comprises:

an I electrode assembly pair or an I electrode assembly sub-array, which corresponds to the nose area of the face;

an II electrode assembly pair or an II electrode assembly sub-array, which corresponds to the forehead area of the face; and an III electrode assembly pair or an III electrode assembly sub-array, which corresponds to the cheek area and the chin area of the face.

In another preferred embodiment, the I electrode assembly pair is in a non-array form.

In another preferred embodiment, the I electrode assembly sub-array comprises ≥3 electrode assemblies.

In another preferred embodiment, the II electrode assembly pair is in a non-array form.

In another preferred embodiment, the II electrode assembly sub-array comprises ≥3 electrode assemblies.

In another preferred embodiment, the III electrode assembly pair is in a non-array form.

In another preferred embodiment, the III electrode assembly sub-array comprises ≥3 electrode assemblies.

In another preferred embodiment, the electrode assembly array comprises:

an I electrode assembly pair or an I electrode assembly sub-array, which corresponds to the nose area of the face;

an II electrode assembly pair or an II electrode assembly sub-array, which corresponds to the forehead area of the face;

an III electrode assembly pair or an III electrode assembly sub-array, which corresponds to the cheek area of the face; and an IV electrode assembly pair or an IV electrode assembly sub-array, corresponds to the chin area of the face.

In another preferred embodiment, the I electrode assembly pair is in a non-array form.

In another preferred embodiment, the I electrode assembly sub-array comprises ≥3 electrode assemblies.

In another preferred embodiment, the II electrode assembly pair is in a non-array form.

In another preferred embodiment, the II electrode assembly sub-array comprises ≥3 electrode assemblies.

In another preferred embodiment, the III electrode assembly pair is in a non-array form.

In another preferred embodiment, the III electrode assembly sub-array comprises ≥3 electrode assemblies.

In another preferred embodiment, the IV electrode assembly pair is in a non-array form.

In another preferred embodiment, the IV electrode assembly sub-array comprises ≥3 electrode assemblies.

In another preferred embodiment, the electrode assembly array comprises:

an I electrode assembly pair or an I electrode assembly sub-array, which corresponds to the nose area of the face;

an II electrode assembly pair or an II electrode assembly sub-array, which corresponds to the forehead area of the face;

an IIIa electrode assembly pair or an IIIa electrode assembly sub-array, which corresponds to the left cheek area and the left chin area of the face; and an IIIb electrode assembly pair or an IIIb electrode assembly sub-array, which corresponds to the right cheek area and the right chin area of the face.

In another preferred embodiment, the I electrode assembly pair is in a non-array form.

In another preferred embodiment, the I electrode assembly sub-array comprises ≥3 electrode assemblies.

In another preferred embodiment, the II electrode assembly pair is in a non-array form.

In another preferred embodiment, the II electrode assembly sub-array comprises ≥3 electrode assemblies.

In another preferred embodiment, the IIIa electrode assembly pair is in a non-array form.

In another preferred embodiment, the IIIa electrode assembly sub-array comprises ≥3 electrode assemblies.

In another preferred embodiment, the IIIb electrode assembly pair is in a non-array form (for example, only comprising two electrode assemblies).

In another preferred embodiment, the IIIb electrode assembly sub-array comprises ≥3 electrode assemblies.

In another preferred embodiment, the electrode assembly array comprises:

an I electrode assembly pair or an I electrode assembly sub-array, which corresponds to the nose area of the face;

an II electrode assembly pair or an II electrode assembly sub-array, which corresponds to the forehead area of the face;

an IIIa electrode assembly pair or an IIIa electrode assembly sub-array, which corresponds to the left cheek area of the face;

an IIIb electrode assembly pair or an IIIb electrode assembly sub-array, which corresponds to the right cheek area of the face; and an IV electrode assembly pair or an IV electrode assembly sub-array corresponds to the chin area of the face.

In another preferred embodiment, the I electrode assembly pair is in a non-array form.

In another preferred embodiment, the I electrode assembly sub-array comprises ≥3 electrode assemblies.

In another preferred embodiment, the II electrode assembly pair is in a non-array form.

In another preferred embodiment, the II electrode assembly sub-array comprises ≥3 electrode assemblies.

In another preferred embodiment, the IIIa electrode assembly pair is in a non-array form.

In another preferred embodiment, the IIIa electrode assembly sub-array comprises ≥3 electrode assemblies.

In another preferred embodiment, the IIIb electrode assembly pair is in a non-array form.

In another preferred embodiment, the IIIb electrode assembly sub-array comprises ≥3 electrode assemblies.

In another preferred embodiment, the IV electrode assembly pair is in a non-array form.

In another preferred embodiment, the IV electrode assembly sub-array comprises ≥3 electrode assemblies.

In another preferred example, among the N electrodes, ≥50% of the electrodes are reconfigurable, and the corresponding electrode and power source pairing can be changed during operation.

Among the N electrodes, preferably ≥70%, more preferably ≥90%, and most preferably ≥95% (such as 100%) of the electrodes are reconfigurable.

In another preferred embodiment, any electrode in the electrode array is connected to a half-bridge drive circuit (HBD) and is driven by the half-bridge drive circuit. In this way, multiple independently controllable power sources and reconfigurable electrodes can be realized.

In another preferred embodiment, the half-bridge drive circuit comprises at least two transistors.

In another preferred embodiment, the half-bridge drive circuit further comprises: a current sensor arranged on the high voltage side; and/or a current sensor arranged on the low voltage side.

In another preferred embodiment, the system further comprises a controller, for controlling the power supply to the electrode assembly array.

In another preferred embodiment, the "controlling the power supply to the electrode assembly array" comprises controlling the voltage of the power supply, the current of the power supply, the waveform of the power supply, the time of the power supply, or a combination thereof.

In another preferred embodiment, the system further comprises: a switch matrix or a multiplexer, which is arranged between the power source and the electrode assembly array.

In another preferred embodiment, the shape of the electrode is selected from the group consisting of a cylinder, a cuboid, and a combination thereof.

In another preferred embodiment, the electrodes have the same or different external surface areas.

In another preferred embodiment, the external surface area of each electrode is: 0.5-50 $cm^2$, preferably 1-40 $cm^2$; more preferably 5-30 $cm^2$.

In another preferred embodiment, the interval distance between two adjacent electrodes is 0.01-5 cm, preferably 0.1-1 cm.

In another preferred embodiment, the material of the electrode is selected from the group consisting of metals, alloys, and conductive carbon materials.

In another preferred embodiment, the system is an electronic facial mask.

In another preferred embodiment, the contact surface formed by the contact layer of the electrode in the electrode assembly array is conformable to the external surface of the face.

In another preferred embodiment, the system configures the electrodes of the electrode assembly array and/or controls the operating state of the electrodes based on the collected data of the face.

In another preferred example, the data is selected from the group consisting of skin moisture content, skin pH, sebum secretion content, skin damage, skin aging, skin roughness, skin bio-resistance analysis and a combination thereof.

In a second aspect of the present invention, it provides a localised transdermal iontophoretic drug delivery method, which comprises the steps of: using the localised transdermal iontophoretic drug delivery system described in the first aspect of the present invention to perform transdermal iontophoretic drug delivery.

In another preferred embodiment, the transdermal iontophoretic drug delivery is the administration to a part selected from group consisting of the face, the neck, the hands, the hands, the legs, the feet, and a combination thereof.

In another preferred embodiment, the method is a cosmetic method.

In another preferred embodiment, the method is a non-therapeutic method.

In another preferred embodiment, the transdermal iontophoretic drug delivery is performed on inanimate objects or bodies.

It should be understood that, within the scope of the present invention, the above-mentioned technical features of the present invention and the technical features specifically described in the following (such as in the Examples) can be combined with each other to form a new or preferred technical solution, that are not described one by one in the specification due to space limitations.

DESCRIPTION OF FIGURES

FIG. 1 shows a schematic diagram of independent current drive assembly. In this example, all electrode assembly pairs and/or electrode assembly sub-arrays can be simultaneously driven.

FIG. 2 shows a schematic diagram of sharing one power source or one current drive assembly using a switch matrix or a multiplexer. In this example, only one electrode assembly pair or one set of electrode assembly sub-arrays can be driven at any time.

FIG. 3 shows a schematic diagram of sharing K power sources or current drive assemblies using a switch matrix or a multiplexer. In this example, only K effective electrode assembly pairs can be driven at any time, wherein the effective electrode pairs can be electrode assembly pairs or electrode assembly sub-arrays.

FIG. 4 shows a traditional mask that uses one pair of electrodes for skin care.

FIG. 6b shows a mask as an example of the present invention, which is divided into a nose area, a forehead area, and a cheek+chin area. In the figure, the electrode assembly pair (1, 1') is for the nose area, and the electrode assembly pair (2, 2') is for the forehead area, and the electrode assembly pair (3, 3') is for the cheek+chin area.

FIG. 6c shows a mask as an example of the present invention, which is divided into a nose area, a forehead area, a cheek area and a chin area. In the figure, the electrode assembly pair (1, 1') is for the nose area, and the electrode assembly pair (2, 2') is for the forehead area, and the electrode assembly pair (3, 3') is for the cheek area, and the electrode assembly pair (4, 4') is for the chin area.

FIG. 6d shows a mask as an example of the present invention, which is divided into a nose area, a forehead area, a left cheek+left chin area, and a right cheek+right chin area. In the figure, the electrode assembly pair (1, 1') is for the nose area, and the electrode assembly pair (2, 2') is for the forehead area, and the electrode assembly pair (3a, 3a') is for the left cheek+left chin area, and the electrode assembly pair (3b, 3b') for the right cheek+right chin area.

FIG. 6e shows a mask as an example of the present invention, which is divided into a nose area, a forehead area, a left cheek area, a right cheek area and a chin area. In the figure, the electrode assembly pair (1, 1') is for the nose area, and the electrode assembly pair (2, 2') is for the forehead area, and the electrode assembly pair (3a, 3a') is for the left cheek area, and the electrode assembly pair (3b, 3b') is for the right cheek area, and the electrode assembly pair (4, 4') is for the chin area.

FIG. 7 shows a schematic diagram of the uniform drug delivery distribution on the face achieved by using the localised transdermal drug delivery controlling of the present invention.

FIG. 8a shows a mask as an example of the present invention, wherein the electrode array is composed of a sub-electrode matrix.

FIG. 8b shows a schematic diagram of a mask as an example of the present invention in which a sub-electrode matrix is formed by four pairs of effective electrodes. The electrode assembly sub-array (1, 1') is for the nose area, and the electrode assembly sub-array (2, 2') is for the forehead area, and the electrode assembly sub-array (3a, 3a') is for the left cheek+left chin area, and the electrode assembly sub-array (3b, 3b') is for the right cheek+right chin area.

FIG. 8c shows a schematic diagram of a mask as an example of the present invention in which a sub-electrode matrix is formed by four pairs of effective electrodes. The electrode assembly pair (1, 1') is for the nose area, and the electrode assembly pair (2, 2') is for the forehead area, and the electrode assembly pair (3a, 3a') is for the left cheek+left chin area, and the electrode assembly pair (3b, 3b') is for the right cheek+right chin area. In addition, the electrodes marked with "x" correspond to wounds and other areas that are not suitable for delivering drug, and the electrodes are set to "not working".

FIG. 9 shows a schematic diagram of a facial mask partly composed of a matrix of sub-electrodes as an example of the present invention, comprising the electrode assembly sub-array (1, 1') for the nose area; the electrode assembly pair (2, 2') for the forehead area; the electrode assembly sub-array (3a, 3a') for the left cheek+left chin area, and the electrode assembly sub-array (3b, 3b') for the right cheek+the right chin area.

FIG. 10 shows that in an example of the present invention, each electrode in the electrode assembly is independently provided with an independent contact layer.

FIG. 11 shows that in an example of the present invention, multiple electrodes in the electrode assembly share one contact layer.

DETAILED DESCRIPTION OF INVENTION

Figure 5:
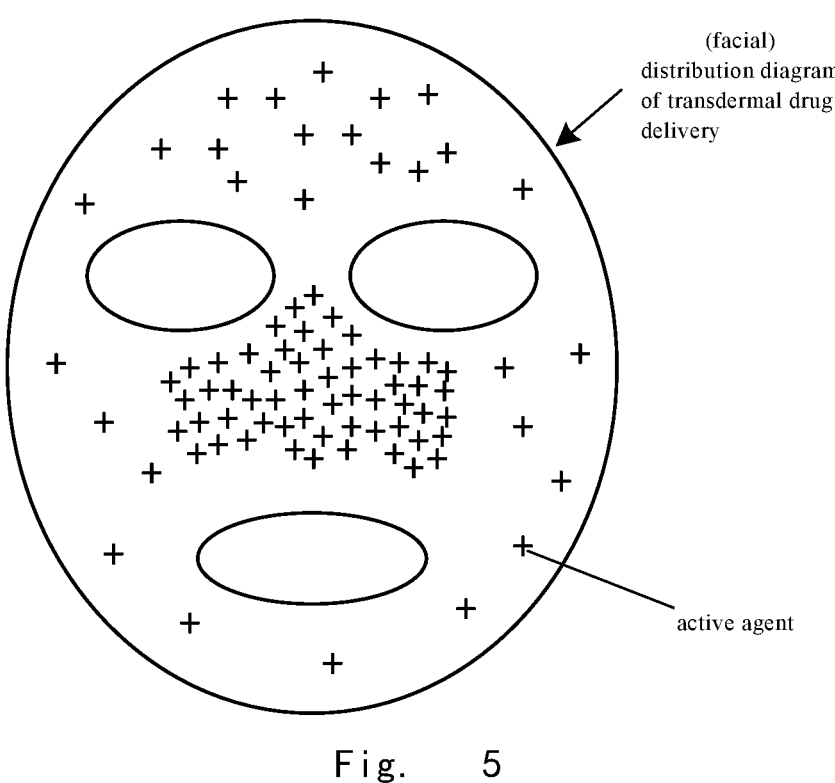
FIG. 5 shows the distribution diagram of transdermal drug delivery using the existing traditional electronic facial mask with only one pair of electrodes to cover the entire face. Due to different skin conditions, the drug delivery current will selectively avoid areas of high resistance, resulting in uncontrolled and uneven distribution of drug delivery.

After extensive and in-depth research, the inventors developed a localised transdermal iontophoretic drug delivery system for the first time, which can locally control (or regulate) many different parameters such as the amount of transdermal drug delivery, the depth of transdermal drug delivery and the speed of transdermal drug delivery. In terms of structure, the localised transdermal iontophoretic drug delivery system of the present invention adopts a special electrode assembly array (the array with multiple electrodes), which can be based on factors such as the moisture content, skin pH, and sebum secretion content of the user's skin, and accurately and efficiently control the amount of transdermal drug delivery, the depth of transdermal drug delivery and the speed of transdermal drug delivery, so as to achieve accurate or personalized transdermal drug delivery or cosmetic. The present invention has been completed on this basis.

Terms

As used herein, the term "electrode assembly" refers to an assembly consisting of an electrode and the corresponding skin contact layer.

As used herein, the term "electrode assembly pair" refers to a pair of assembly consisting of two electrode assemblies.

As used herein, the term "electrode assembly array" refers to an array composed of at least 3 electrode assemblies, or more than one pair of electrode assemblies.

As used herein, the term "electrode assembly sub-array" refers to a sub-array composed of at least 3 electrode assemblies, or more than one pair of electrode assemblies. One or more sub-arrays can form a large array.

As used herein, "C(N, 2)" refers to the total number of combination of any 2 elements selected from N elements, namely $(N!)/(2!*(N-2)!)$.

Localised Transdermal Iontophoretic Drug Delivery System

The present invention provides a localised transdermal iontophoretic drug delivery system, which comprises:

(a) an electrode assembly array, wherein the electrode assembly array comprises N electrode assemblies, and $N \geq 3$; and each electrode assembly comprises one electrode; and (b) M power sources, wherein the power sources are used for supplying current to the corresponding electrodes or electrode pairs, wherein M is a positive integer from 1 to C (N, 2), wherein C (N, 2) represents a combination of "N select 2";

wherein, at least two electrodes in the electrode assembly array are provided with a medium containing an electrically charged active agent, and the current pushes the active agent to the skin layer at a time period during which the current has the same polarity as that of the active agent.

Wherein, if the number of electrodes N is an even number, and the number of power supplies M can be a positive integer ranging from 2 to N/2, and the shape of the electrode is selected from the group consisting of a cylinder, a cuboid and a combination thereof.

In the present invention, the electrodes have the same or different external surface areas. Typically, the external surface area of one or more or all of the electrodes is 0.5-50 cm², preferably 1-40 cm²; more preferably 5-30 cm².

In the present invention, the internal distance between two adjacent electrodes is not particularly limited, and is usually 0.01-5 cm, preferably 0.1-1 cm.

In the present invention, the electrodes can be made of conventional electrode materials. Representative electrode materials include (but are not limited to): metals, alloys, conductive carbon materials, or combinations thereof.

The system of the present invention further comprises a controller for controlling the power supply to the electrode assembly array. The "controlling the power supply to the electrode assembly array" comprises controlling the voltage of the power supply, the current of the power supply, the waveform of the power supply, the time of the power supply, or a combination thereof.

In addition, the system of the present invention may further comprise: one or more switch matrixes or multiplexers, which are arranged between the power sources and the electrode assembly array.

Preferably, among the N electrodes, ≥50% of the electrodes are reconfigurable, and the corresponding electrode and power source pairing can be changed during operation; preferably ≥70%, more preferably ≥90%, most preferably ≥95% (such as 100%) electrodes are reconfigurable.

The system of the present invention can be made into different forms according to application occasions. A typical form is the facial mask form, that is, the electronic facial mask form. In the present invention, the electronic facial mask can cover all, most, or part of the face area.

Taking human as an example, the face area mainly comprises the following sub-areas, such as the nose area, the forehead area, the cheek area, and the chin area. Among them, each sub-area can be further divided into a left sub-area and a right sub-area.

Power Supply Implementation Mode

In the present invention, the power source is used for supplying power to the electrode assembly array in a variety of modes.

Typically, the M power sources are used for supplying power to the electrode assembly array in the following modes:

Mode 1: One or more power sources; and multiple current drive assemblies;

Mode 2: One or more power sources; and a switch matrix or a multiplexer;

Mode 3: One or more power sources; one or more current drive assemblies; and a switch matrix or a multiplexer.

Wherein, the power sources simultaneously supplies current to the corresponding electrodes or electrode pairs.

The power sources successively supplies current to the corresponding electrodes or electrode pairs.

The power sources can supply current to the corresponding electrode or electrode pair at different time periods.

In the present invention, the current used in the system of the present invention is a direct current, an alternating current, or both.

In the present invention, either direct current or alternating current can be used to safely, effectively and accurately achieve transdermal drug delivery or cosmetic purposes by setting appropriate parameters such as voltage, current, and electrification time according to needs In the present invention, for alternating current, it is advisable to have one or more characteristics selected from the following group:

(i) the period is 1 second to 30 minutes, preferably from 1 second to 15 minutes, more preferably from 1 second to 10 minutes, and most preferably from 1 second to 5 minutes;

(ii) the waveform is a basic waveform between the maximum value and the minimum value, comprising a climbing time period, during which the current increases from the minimum value to the maximum value, or decreases from the maximum value to the minimum value; and (iii) the duty ratio is 5%-95%, preferably 10-80%, more preferably 20-70%.

Preferably, when the system of the present invention is working, the current between any working electrode pair should be 0.01-4 mA.

Electrode Assembly

Each electrode assembly described comprises a corresponding contact layer; and the contact layer is used to store a medium containing an active agent and be connected with electrode fluid.

In the present invention, as shown in FIG. 10, each electrode may be provided with an independent contact layer; or as shown in FIG. 11, multiple electrodes sharing one contact layer are used.

Electrode Assembly Array

Each electrode assembly in the electrode assembly array comprises a connector, and the connector connects the electrode assembly to the corresponding power source. Wherein, the connector connects the electrode assembly to the corresponding current drive assembly, and the connector connects the electrode assembly to the corresponding switch matrix or multiplexer.

In an example of the present invention, represented by FIG. 6c, the electrode assembly array may further comprises:

an I electrode assembly pair or an I electrode assembly sub-array, which corresponds to the nose area of the face; and an II electrode assembly pair or an II electrode assembly sub-array, which corresponds to the forehead area, cheek area and chin area of the face.

Wherein, the I electrode assembly pair is in a non-array form, and the I electrode assembly sub-array comprises ≥3 electrode assemblies.

The II electrode assembly pair is in a non-array form, and the II electrode assembly sub-array comprises ≥3 electrode assemblies.

In an example of the present invention, represented by FIG. 6b, the electrode assembly array may comprise:

an I electrode assembly pair or an I electrode assembly sub-array, which corresponds to the nose area of the face;

an II electrode assembly pair or an II electrode assembly sub-array, which corresponds to the forehead area of the face; and an III electrode assembly pair or an III electrode assembly sub-array, which corresponds to the cheek area and the chin area of the face.

Wherein, the I electrode assembly pair is in a non-array form, and the I electrode assembly sub-array comprises ≥3 electrode assemblies.

The II electrode assembly pair is in a non-array form, and the II electrode assembly sub-array comprises ≥3 electrode assemblies.

The III electrode assembly pair is in a non-array form, and the III electrode assembly sub-array comprises ≥3 electrode assemblies.

In an example of the present invention, represented by FIG. 6c, the electrode assembly array may further comprises:

an I electrode assembly pair or an I electrode assembly sub-array, which corresponds to the nose area of the face;

an II electrode assembly pair or an II electrode assembly sub-array, which corresponds to the forehead area of the face;

an III electrode assembly pair or an III electrode assembly sub-array, which corresponds to the cheek area of the face; and an IV electrode assembly pair or an IV electrode assembly sub-array corresponds to the chin area of the face.

Wherein, the I electrode assembly pair is in a non-array form, and the I electrode assembly sub-array comprises ≥3 electrode assemblies.

The II electrode assembly pair is in a non-array form, and the II electrode assembly sub-array comprises ≥3 electrode assemblies.

The III electrode assembly pair is in a non-array form, and the III electrode assembly sub-array comprises ≥3 electrode assemblies.

The IV electrode assembly pair is in a non-array form, and the IV electrode assembly sub-array comprises ≥3 electrode assemblies.

In an example of the present invention, represented by FIG. 6d, the electrode assembly array may also comprise:

an I electrode assembly pair or an I electrode assembly sub-array, which corresponds to the nose area of the face;

an II electrode assembly pair or an II electrode assembly sub-array, which corresponds to the forehead area of the face;

an IIIa electrode assembly pair or an IIIa electrode assembly sub-array, which corresponds to the left cheek area and left chin area of the face; and an IIIb electrode assembly pair or an IIIb electrode assembly sub-array, which corresponds to the right cheek area and the right chin area of the face.

Wherein, the I electrode assembly pair is in a non-array form, and the I electrode assembly sub-array comprises ≥3 electrode assemblies;

the II electrode assembly pair is in a non-array form, and the II electrode assembly sub-array comprises ≥3 electrode assemblies.

The IIIa electrode assembly pair is in a non-array form, and the IIIa electrode assembly sub-array comprises ≥3 electrode assemblies.

The IIIb electrode assembly pair is in a non-array form, and the IIIb electrode assembly sub-array comprises ≥3 electrode assemblies.

In an example of the present invention, represented by FIG. 6e, the electrode assembly array further comprises:

an I electrode assembly pair or an I electrode assembly sub-array, which corresponds to the nose area of the face;

an II electrode assembly pair or an II electrode assembly sub-array, which corresponds to the forehead area of the face;

an IIIa electrode assembly pair or an IIIa electrode assembly sub-array, which corresponds to the left cheek area of the face;

an IIIb electrode assembly pair or an IIIb electrode assembly sub-array, which corresponds to the right cheek area of the face; and an IV electrode assembly pair or an IV electrode assembly sub-array corresponds to the chin area of the face.

Wherein, the I electrode assembly pair is in a non-array form, and the I electrode assembly sub-array comprises ≥3 electrode assemblies.

the II electrode assembly pair is in a non-array form, and the II electrode assembly sub-array comprises ≥3 electrode assemblies.

The IIIa electrode assembly pair is in a non-array form, and the IIIa electrode assembly sub-array comprises ≥3 electrode assemblies.

The IIIb electrode assembly pair is in a non-array form, and the IIIb electrode assembly sub-array comprises ≥3 electrode assemblies.

The IV electrode assembly pair is in a non-array form, and the IV electrode assembly sub-array comprises ≥3 electrode assemblies.

Half-Bridge Drive Circuit (HBD)

In an example of the present invention, represented by FIG. 1, any electrode in the electrode array is connected to a half-bridge drive circuit (HBD) and is driven by the half-bridge drive circuit. In this way, multiple independently controllable power sources and reconfigurable electrodes can be realized.

In another preferred embodiment, the half-bridge drive circuit comprises at least two transistors.

In another preferred embodiment, the half-bridge drive circuit further comprises: a current sensor arranged on the high voltage side; and/or a current sensor arranged on the low voltage side.

Facial Mask

The system of the present invention is an electronic facial mask, and the contact surface formed by the contact layer of the electrode in the electrode assembly matrix is conformable to the external surface of the face.

In the present invention, the system configures the electrodes of the electrode assembly matrix and/or controls the operating state of the electrodes based on the collected data of the face. And the data is selected from the group consisting of skin moisture content, skin pH, sebum secretion content, skin damage, skin aging, skin roughness, skin bio-resistance analysis and a combination thereof.

For convenience of description, the invention is further described below in combination with the attached figures. It should be understood that these figures are not used to limit the scope of the present invention.

The existing facial mask is shown in FIG. 4, which cannot control transdermal drug delivery locally. When a user uses the existing facial mask, due to different skin conditions, the drug delivery current will selectively avoid areas of high resistance, resulting in uncontrolled and uneven distribution of drug delivery. The distribution of the active agent on the face is shown in FIG. 5.

The optimized facial mask of the present invention can be customized for individuals or user groups, and localised transdermal drug delivery control can achieve the uniform drug delivery distribution diagram as shown in FIG. 7.

Figure 6A:
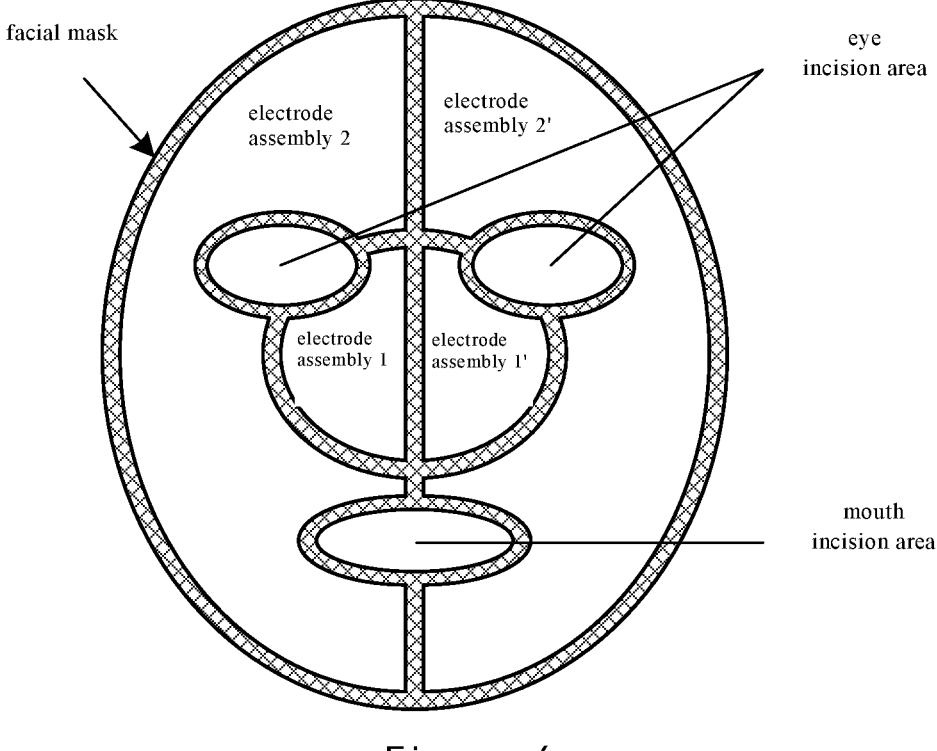
FIG. 6a shows a mask as an example of the present invention, which is divided into a nose area and a forehead+cheek+chin area. In the figure, the electrode assembly pair (1, 1') is for the nose area, and the electrode assembly pair (2, 2') is for the forehead+cheeks+chin area.

An exemplary mask of the present invention is shown in FIG. 6*a*. The distribution of electrode assemblies in the mask is divided into an electrode assembly pair (1, 1') for the nose area, and an electrode assembly pair (2, 2') for the forehead+cheek+chin area.

An exemplary mask of the present invention is shown in FIG. 6*b*. The distribution of electrode assemblies in the mask is divided into an electrode assembly pair (1, 1') for the nose area, an electrode assembly pair (2, 2') for the forehead area, and an electrode assembly pair (3, 3') for the cheek+chin area.

An exemplary mask of the present invention is shown in FIG. 6*c*. The distribution of electrode assemblies in the mask is divided into an electrode assembly pair (1, 1') for the nose area, an electrode assembly pair (2, 2') for the forehead area, and an electrode assembly pair (3, 3') for the cheek area, and an electrode assembly pair (4, 4') for the chin area.

An exemplary mask of the present invention is shown in FIG. 6*d*. The distribution of electrode assemblies in the mask is divided into an electrode assembly pair (1, 1') for the nose area, an electrode assembly pair (2, 2') for the forehead area, and an electrode assembly pair (3*a*, 3*a'*) for the left cheek+left chin area, and an electrode assembly pair (3*b*, 3*b'*) for the right cheek+right chin area.

An exemplary mask of the present invention is shown in FIG. 6*e*. The distribution of electrode assemblies in the mask is divided into an electrode assembly pair (1, 1') for the nose area, an electrode assembly pair (2, 2') for the forehead area, and an electrode assembly pair (3*a*, 3*a'*) is for the left cheek area, an electrode assembly pair (3*b*, 3*b'*) for the right cheek area, and an electrode assembly pair (4, 4') for the chin area.

An exemplary mask of the present invention is shown in FIG. 8*a*. The electrode assembly array in the mask is composed of an electrode assembly sub-array.

The main advantages of the present invention include:
(a) it can precisely control the amount of transdermal drug delivery, the depth of transdermal drug delivery and/or the speed of transdermal drug delivery to a predetermined area, so as to achieve precise and uniform drug delivery (or deliver of cosmetic active ingredients).
(b) when there are areas (such as wounds) on the user's face that are not suitable for drug delivery, other areas can still be delivered, and adverse effects on the user's unsuitable areas for drug delivery can be avoided to the greatest extent.

The present invention will be further explained below in conjunction with specific examples. It should be understood that these examples are only used to illustrate the present invention and not to limit the scope of the present invention. The experimental methods that do not indicate specific conditions in the following examples usually follow the conventional conditions or the conditions suggested by the manufacturer. Unless otherwise stated, percentages and parts are calculated by weight.

Example 1

Localised Transdermal Iontophoretic Drug Delivery System No. 1

In this example, the localised transdermal iontophoretic drug delivery system comprised an electrode assembly array matrix, and the electrode assembly array, as shown in FIG. 8*a*, comprised 56 electrode assemblies, wherein each electrode assembly comprised an electrode, a skin contact layer, and a connector.

In addition, any electrode in the electrode array was connected to an HBD (the mode in FIG. 1) and was driven by the half-bridge drive circuit. In this way, multiple independently controllable power supplies and reconfigurable electrodes can be realized. In this example, the current between any two electrodes can be controlled, and can be grouped into 1540 (2 selected from 56) different current sources.

The transdermal iontophoretic drug delivery system adopted the mask structure shown in FIG. 8*a*. When used, different effective electrode assembly pairs can be formed according to different skin conditions (the data of skin moisture content, skin pH, sebum secretion content, skin damage, skin aging, skin roughness, or skin bio-resistance analysis) of users. Among them, as shown in FIG. 8*b*, a common effective electrode assembly distribution was an effective electrode assembly pair (1, 1') for the nose area; an effective electrode assembly pair (2, 2') for the forehead area; an effective electrode assembly pair (3*a*, 3*a'*) for the left cheek+left chin area; and an effective electrode assembly pair (3*b*, 3*b'*) for the right cheek+right chin area.

The localised transdermal iontophoretic drug delivery system can overcome the uncontrollable and uneven drug delivery caused by the different skin conditions the selective avoidance of areas of high resistance by the drug delivery current, and can achieve uniform active agent distribution as shown in FIG. 7. Localised control can also target different areas to achieve different levels of drug delivery, that is, to optimize the distribution of active doses on the user's face.

In addition, if the user has a wound on the skin, the independently controlled electrode array can also selectively avoid the wound. As shown in FIG. 8*c*, the electrodes marked with "x" correspond to wounds and other areas that are not suitable for drug delivery, and the electrodes marked with "x" are set to "not working" while other electrodes are set to working.

Example 2

Localised Transdermal Iontophoretic Drug Delivery System No. 2

In this example, the localised transdermal iontophoretic drug delivery system comprised an electrode assembly array, and the electrode assembly array, as shown in FIG. 6*d*, comprised 8 electrode assemblies, wherein each electrode assembly comprised an electrode, a skin contact layer, and a connector.

In addition, the electrodes in the electrode array were connected through two (4:1) multiplexers (the mode in FIG. 2) and shared one power source. Among them, electrode assemblies 1, 2, 3*a*, and 3*b* were connected to the first (4:1) multiplexer, and electrode assemblies 1', 2', 3*a'*, and 3*b'* were connected to the second (4:1) multiplexer. In this example, reducing the number of circuit components was one of the main design goals.

As shown in FIG. 6*d*, the effective electrode assembly pair (1, 1') was for the nose area; and the effective electrode assembly pair (2, 2') was for the forehead area; and the effective electrode assembly pair (3*a*, 3*a'*) was for the left cheek+left chin area; and the effective electrode assembly pair (3*b*, 3*b'*) was for the right cheek+right chin area.

The transdermal iontophoretic drug delivery system adopted the mask structure as shown in FIG. 6*d*, wherein the contact surface formed by the contact layer of the electrode in the mask electrode assembly matrix was conformable to the external surface of the face. In the skin care, according to the data of skin moisture content, skin pH, sebum secretion content, skin damage, skin aging, skin roughness, skin bio-resistance analysis collected from different areas of the face, the amount of transdermal drug delivery, the depth of transdermal drug delivery and the speed of transdermal drug delivery can be efficiently controlled. The electrode assembly distribution of this example can effectively achieve the uniform active agent distribution as shown in FIG. 7. Localised control can also target different areas to achieve different levels of drug delivery, that is, to optimize the distribution of active doses on the user's face.

Comparative Example 1

The existing facial mask is shown in FIG. 4. The mask used a pair of electrodes, which cannot achieve locally controlled transdermal drug delivery. When users used the existing mask, transdermal drug delivery was not targeted.

In the skin care, it was impossible to personally control different skin types in different areas of the face. The existing system can achieve the active agent distribution as shown in FIG. 5. Due to different skin conditions, the drug delivery current would selectively avoid areas of high resistance, resulting in uncontrolled and uneven distribution of drug delivery.

All documents mentioned in the present invention are cited as references in this application, as if each document was individually cited as a reference. In addition, it should be understood that after reading the above teaching content of the present invention, those skilled in the art can make various changes or modifications to the present invention, and these equivalent forms also fall within the scope defined by the appended claims of the present application.

The invention claimed is:

1. A localized transdermal iontophoretic drug delivery system, wherein the system comprises:
   - (a) an electrode assembly array, wherein the electrode assembly array comprises N electrode assemblies, and N≥3; each electrode assembly comprises one or more electrodes, the number of electrodes is an even number, and the one or more electrodes comprise a contact layer for contacting the electrode with a skin layer of a face having an external surface; and
   - (b) M power sources, wherein each power source corresponds to an electrode of the electrode assembly array or a pair of electrodes of the electrode assembly array, and each power source is used for supplying a current to the corresponding electrode of the electrode assembly array or the pair of the corresponding electrodes of the electrode assembly array, wherein M is a positive integer from 2 to C (N, 2), wherein C (N, 2) is defined as $(N!)/(2!*(N-2)!)$;
   - wherein, at least two electrodes in the electrode assembly array are provided with a medium containing an electrically charged active agent, and the current supplied by one of the M power sources pushes the active agent to the skin layer during a time period in which the current has the same polarity as the active agent;
   - wherein the one or more electrodes in the electrode assembly array is connected to a half-bridge drive circuit (HBD) and is driven by the HBD, ≥50% of the electrodes of the N electrode assemblies are reconfigurable, and the corresponding electrode and power source pairing can be changed during operation;
   - wherein the HBD further comprises: a current sensor arranged on the high voltage side; and/or a current sensor arranged on the low voltage side;

wherein the current supplied to at least two of the electrodes in the electrode assembly array are independently controlled by the HBD or the M power sources,
wherein the system is an electronic facial mask, wherein a contact surface formed by the contact layer of the electrodes in the electrode assembly array is conformable to the external surface of the face;
and wherein the system configures the electrodes of the electrode assembly array and/or controls the operating state of the electrodes based on a collected data of the face.

2. The system of claim 1, wherein the M power sources are used for supplying power to the electrode assembly array through multiple current drive assemblies.

3. The system of claim 1, wherein each power source simultaneously supplies current to the corresponding electrode or the corresponding electrode pair.

4. The system of claim 1, wherein each power source can supply current to the corresponding electrode or the corresponding electrode pair at different time periods.

5. The system of claim 1, wherein each electrode assembly that is provided with the medium comprises a corresponding contact layer; wherein, the contact layer is used to store the medium containing the active agent and is connected with electrode fluid.

6. The system of claim 1, wherein the electrode assemblies that are provided with the medium share one contact layer; wherein, the contact layer is used to store medium containing the active agent and is connected with electrode fluid.

7. The system of claim 1, wherein the electrodes of the electrode assemblies of the electrode assembly array form:
   - a first electrode assembly pair or an I electrode assembly sub-array, which corresponds to a nose area of the face;
   - a second electrode assembly pair or an II electrode assembly sub-array, which corresponds to a forehead area of the face;
   - a third electrode assembly pair or an IIIa electrode assembly sub-array, which corresponds to a left cheek area and a left chin area of the face; and
   - a fourth electrode assembly pair or an IIIb electrode assembly sub-array, which corresponds to a right cheek area and a right chin area of the face.

8. The system of claim 1, wherein the HBD comprises at least two transistors.

9. The system of claim 1, wherein the system further comprises: a switch matrix or a multiplexer, which is arranged between the power sources and the electrode assembly array.

10. The system of claim 1, wherein the external surface area of each electrode is between 0.5 $cm^2$ to 50 $cm^2$.

11. The system of claim 1, wherein the collected data is selected from the group consisting of skin moisture content, skin pH, sebum secretion content, skin damage, skin aging, skin roughness, skin bio-resistance analysis and a combination thereof.

12. The system of claim 1, wherein the electrode assembly array comprises:
   - a first electrode assembly pair or a first electrode assembly sub-array, which corresponds to a nose area of the face; and
   - a second electrode assembly pair or a second electrode assembly sub-array, which corresponds to a forehead area, a cheek area and a chin area of the face; wherein the first electrode assembly pair is in a non-array form; or the first electrode assembly sub-array comprises ≥3 electrode assemblies.

13. The system of claim 1, wherein the electrode assembly array comprises:

a first electrode assembly pair or a first electrode assembly sub-array, which corresponds to a nose area of the face;

a second electrode assembly pair or a second electrode assembly sub-array, which corresponds to a forehead area of the face; and a third electrode assembly pair or a third electrode assembly sub-array, which corresponds to a cheek area and a chin area of the face; wherein the first electrode assembly pair, the second electrode assembly pair and the third electrode assembly pair are each independently in a non-array form; or the first electrode assembly sub-array, the second electrode assembly sub-array and the third electrode assembly sub-array each independently comprise ≥3 electrode assemblies.

14. The system of claim 1, wherein the electrode assembly array comprises:

a first electrode assembly pair or a first electrode assembly sub-array, which corresponds to a nose area of the face;

a second electrode assembly pair or a second electrode assembly sub-array, which corresponds to a forehead area of the face;

a third electrode assembly pair or a third electrode assembly sub-array, which corresponds to a cheek area of the face; and a fourth electrode assembly pair or a fourth electrode assembly sub-array, which corresponds to a chin area of the face; wherein the first electrode assembly pair, the second electrode assembly pair, the third electrode assembly pair and the fourth electrode assembly pair are each independently in a non-array form; or the first electrode assembly sub-array, the second electrode assembly sub-array, the third electrode assembly sub-array and the fourth electrode assembly sub-array each independently comprise ≥3 electrode assemblies.

15. The system of claim 1, wherein the electrode assembly array comprises:

a first electrode assembly pair or a first electrode assembly sub-array, which corresponds to a nose area of the face;

a second electrode assembly pair or a second electrode assembly sub-array, which corresponds to a forehead area of the face;

a third electrode assembly pair or a third electrode assembly sub-array, which corresponds to a left cheek area of the face;

a fourth electrode assembly pair or a fourth electrode assembly sub-array, which corresponds to a right cheek area of the face; and a fifth electrode assembly pair or a fifth electrode assembly sub-array, which corresponds to a chin area of the face; wherein the first electrode assembly pair, the second electrode assembly pair, the third electrode assembly pair, the fourth electrode assembly pair and the fifth electrode assembly pair are each independently in a non-array form; or the first electrode assembly sub-array, the second electrode assembly sub-array, the third electrode assembly sub-array, the fourth electrode assembly sub-array and the fifth electrode assembly sub-array each independently comprise ≥3 electrode assemblies.

16. The system of claim 1, wherein each of the one or more electrodes in the electrode assembly array is connected to the HBD and is driven by the HBD.

17. The system of claim 1, wherein each electrode assembly comprises two or more electrodes.

18. The system of claim 1, wherein the HBD is connected to the same power source or different power sources.

19. A localized transdermal iontophoretic drug delivery method, comprising the steps of: using the localized transdermal iontophoretic drug delivery system of claim 1 to perform transdermal iontophoretic drug delivery.

20. The method of claim 19, wherein the method is a non-therapeutic method.

21. The method of claim 19, wherein the localized transdermal iontophoretic drug delivery method is performed on inanimate objects or bodies.

* * * * *